United States Patent
Nord

[11] Patent Number: 6,074,403
[45] Date of Patent: Jun. 13, 2000

[54] SUTURE RETRIEVER

[75] Inventor: Keith D. Nord, Jackson, Tenn.

[73] Assignee: Arthrex, Inc., Naples, Fla.

[21] Appl. No.: 09/178,416

[22] Filed: Oct. 26, 1998

Related U.S. Application Data

[60] Provisional application No. 60/063,444, Oct. 29, 1997.

[51] Int. Cl.[7] .................................................. A61B 17/04

[52] U.S. Cl. ............................................................ 606/144

[58] Field of Search .................................. 606/144, 148, 606/205–211, 139

[56] References Cited

U.S. PATENT DOCUMENTS 5,181,919  1/1993  Bergman et al. ........................ 606/144

*Primary Examiner*—Michael Buiz
*Assistant Examiner*—Antony King
*Attorney, Agent, or Firm*—Ostrolenk, Faber, Gerb & Soffen, LLP

[57] ABSTRACT

An instrument for retrieving suture within a patient has a shaft with proximal and distal ends. The distal end terminates in a sharp tip. An opening in the shaft is provided proximal to the sharp tip. A jaw disposed on the shaft captures suture within the opening in the shaft. A hand mechanism disposed on the proximal end of the shaft opens and closes the jaw.

22 Claims, 1 Drawing Sheet

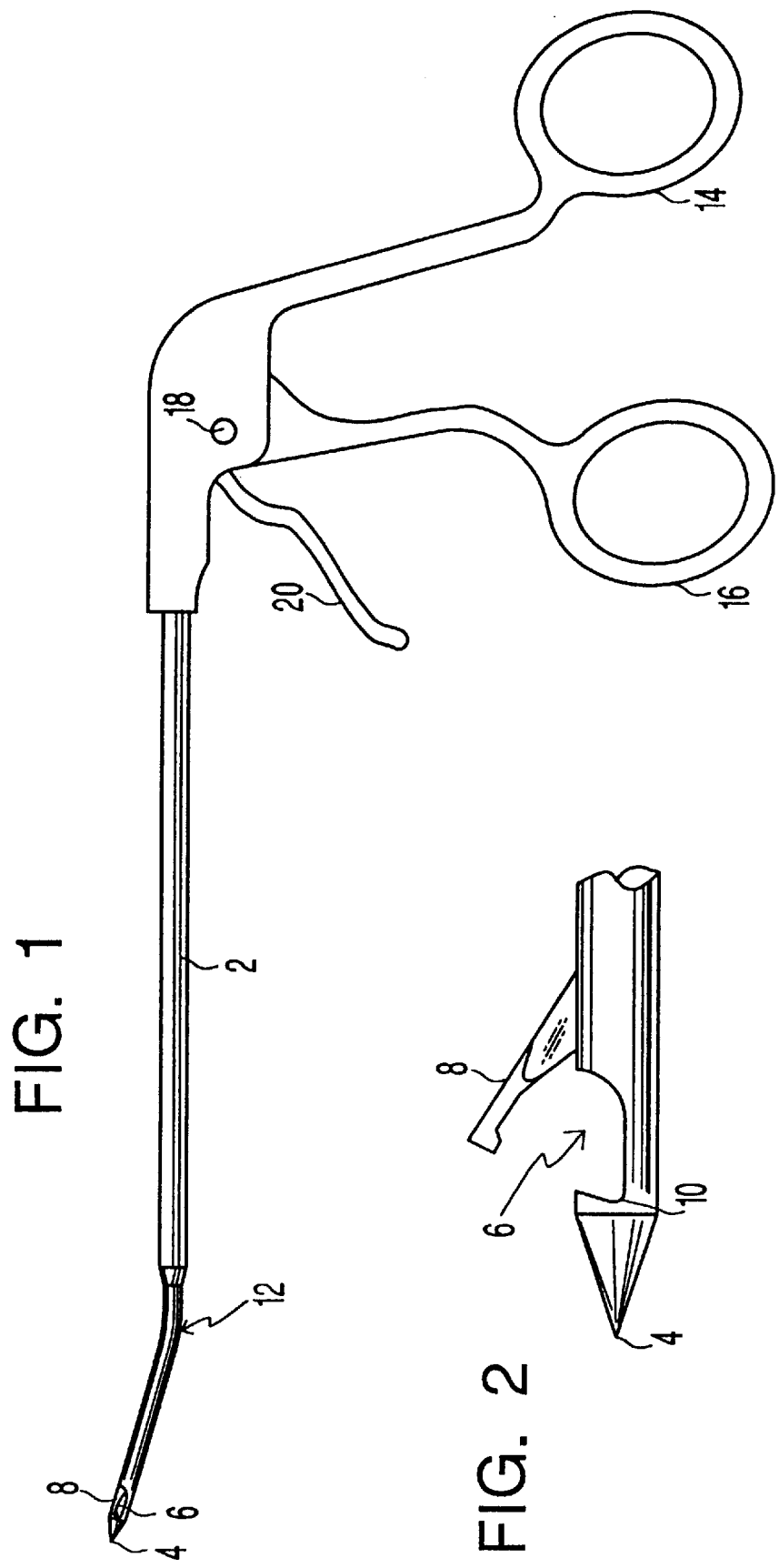

SUTURE RETRIEVER

This application claims the benefit of U.S. Provisional Application Serial No. 60/063,444, filed on Oct. 29, 1997, the disclosure of which is incorporated herein by reference.

BACKGROUND OF THE INVENTION

1. Field of the Invention

The present invention relates to endoscopic surgical methods and devices, and more specifically to methods and apparatus for manipulation of suture during endoscopic surgical procedures.

2. Description of the Related Art

Endoscopic suturing techniques and instruments have been developed in order to facilitate the suturing of tissue during endoscopic surgical procedures. The term "endoscopy" encompasses arthroscopy, laparoscopy, hysteroscopy, etc., and endoscopic surgery involves the performance of surgical procedures within a patient's body through small openings as opposed to conventional open surgery through large incisions. Access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to tie sutures endoscopically. For example, some procedures enable the surgeon to pass suture material through selected tissue, form a surgical knot extracorporeally and then move the knot with a knot pusher through the portal or cannula into position adjacent the desired tissue to be sutured. Some instruments used to pass the suture incorporate a hollow needle provided with some means, often a wire loop, to guide suture through the tissue pierced by the needle.

SUMMARY OF THE INVENTION

The present invention provides a hand instrument for retrieving suture within a patient. The suture retriever includes a shaft having a proximal end and a distal end, the distal end terminating in a sharp tip. An opening in the shaft is disposed proximal to the sharp tip. A hinged jaw disposed on the shaft closes to capture suture within the opening in the shaft. A hand mechanism, preferably including finger loops, is disposed on the proximal end of the shaft for opening and closing the jaw.

Advantageously, the opening is sized such that when the jaw is closed, suture captured within the opening is allowed to slide freely as the suture grasper passes through soft tissue. The opening preferably has a notched or sloped distal face, such that suture captured in the opening tends to slide into the notch, rather than out of the opening toward the jaw.

For ease of use in various surgical situations, the instrument can be formed with a bend in the shaft, preferably proximal to the opening in the shaft. In particular for rotator cuff and glenoid labral repair, the opening is disposed on an upper side of the shaft, and the shaft is bent upward at about a 15° angle. Bends in other directions and of differing degrees can be provided, such as side bends of 15°, 30°, 45°, and 60°. A straight shafted instrument also can be provided.

The instrument is provided so as to pass through a 6 mm cannula, the jaw closing flush with the outer surface of the shaft. Advantageously, the shaft is tapered toward the distal end such that the sharp tip has a 2.5 mm diameter for ease of penetrating soft tissue.

A method of endoscopically retrieving suture disposed within a patient using the instrument of the present invention includes closing the jaw using the hand mechanism and inserting the shaft of the instrument into the patient. The tissue to be sutured is penetrated with the sharp tip, and the jaw is opened. The opening in the shaft is positioned proximate a piece of suture disposed in the patient, and the jaw is closed to capture the suture within the opening. As the instrument is retrograded, the captured suture is pulled back through the tissue, the suture being allowed to slide freely through the closed opening to prevent damage to the suture.

Preferably, the jaw can be locked in the closed position. Accordingly, during instrument insertion for example, it is not necessary for the surgeon to maintain hand position at the finger loops of the instrument as the instrument is guided through tissue.

Other features and advantages of the present invention will become apparent from the following description of the invention which refers to the accompanying drawings.

BRIEF DESCRIPTION OF THE DRAWINGS

FIG. 1 is a side elevation of a suture retriever according to the present invention.

FIG. 2 is a detail of the distal tip of the suture retriever according to the present invention.

DETAILED DESCRIPTION OF THE DRAWINGS

Referring initially to FIG. 1, a suture retriever is shown according to a preferred embodiment of the present invention. The suture retriever includes a shaft 2 having a sharp distal tip 4. An opening 6 is formed in the shaft 2. A hinged jaw 8, shown in the closed position in FIG. 1, covers the opening 6.

In the closed position, the jaw 8 occupies a portion of the opening 6, and the outer surface of the jaw 8 forms a smooth surface contiguous with the outer surface of the shaft 2. A strand of suture captured in the opening, with the jaw closed, is free to slide within the opening as the suture retriever is pulled through soft tissue, thus protecting the suture from damage. In the open position the jaw 8 provides access to the opening 6 for capturing suture, as shown in detail FIG. 2.

The opening 6 preferably has a notch 10 formed on the distal face of the opening, such that suture captured within the opening tends to slide toward the bottom of the opening, rather than sliding up and out toward the jaw, as the instrument is pulled back through soft tissue.

Shaft 2 is provided with a 15° upward bend 12, according to a preferred embodiment of the present invention. The 15° upward bend positions the tip at the proper angle for passing through the glenoid labrum.

A hand mechanism is disposed on the proximal end of the shaft 2 by which the jaw 8 is operated. The hand mechanism includes a stationary thumb loop 14 and a moveable finger loop 16 secured by pivot 18. Moveable finger loop 16 actuates closing and opening of jaw 8. A camlock mechanism operated by lever 20 locks the jaw in a closed position, for example, to facilitate insertion of the suture retriever through tissue.

The instrument preferably is designed to pass through a 6 mm cannula. The shaft 2 steps down from a maximum diameter of about 3.9 mm to a diameter of 2.5 mm near the sharp tip 4 for ease of penetration through tissue.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An instrument for retrieving suture within a patient, the instrument comprising:

a shaft having a proximal end and a distal end;

an opening in the shaft disposed proximal to the distal end;

a pivotably operable jaw disposed on the shaft for capturing suture within the opening in the shaft, the jaw having a distal end disposed proximal to the distal end of the shaft when the jaw is in a closed position; and a hand mechanism disposed on the proximal end of the shaft for opening and closing the jaw.

2. The instrument of claim 1, wherein the opening has a size such that when the jaw is closed, captured suture is allowed to slide freely within the opening.

3. The instrument of claim 1, wherein the shaft has a bend proximal to the opening in the shaft.

4. The instrument of claim 3, wherein the hand mechanism is disposed on a lower side of the shaft and the opening is disposed on an upper side of the shaft.

5. The instrument of claim 4, wherein the shaft is bent upward away from the hand mechanism.

6. The instrument of claim 1, wherein the shaft is tapered substantially proximal to the distal end such that a distal portion of the shaft has a diameter that is smaller than a diameter of a proximal portion of the shaft.

7. The instrument of claim 1, wherein the jaw closes flush with an outer surface of the shaft.

8. The instrument of claim 1, wherein the hand mechanism includes a moveable finger loop and a stationary thumb loop.

9. The instrument of claim 1, further comprising a locking mechanism for maintaining the jaw in a fixed position.

10. The instrument of claim 1, further comprising a locking mechanism for maintaining the jaw in a closed position.

11. The instrument of claim 1, further comprising a notch formed on a distal face of the opening for retaining suture captured within the opening and urging the suture away from the jaw as the instrument is drawn proximally.

12. The instrument of claim 1, wherein the opening is formed in a side of the shaft.

13. The instrument of claim 1, wherein the jaw covers the opening in the closed position.

14. The instrument of claim 1, wherein the jaw at least partially occludes the opening when the jaw is in the closed position.

15. The instrument of claim 1, wherein when the jaw closes, an outer surface of the jaw forms a surface that is smooth and contiguous with an outer surface of the shaft.

16. The instrument of claim 1, wherein the jaw is hinged to the shaft proximally.

17. The instrument of claim 1, wherein the jaw opens distally.

18. The instrument of claim 1, wherein the distal end of the shaft terminates in a sharp tip.

19. A method of endoscopically retrieving suture disposed within a patient using an instrument having a shaft having a proximal end and a distal end, an opening in the shaft disposed proximal to the distal end, a jaw disposed on the shaft for capturing suture within the opening in the shaft, the jaw having a distal end disposed proximal to the distal end of the shaft when the jaw is in a closed position, and a hand mechanism disposed on the proximal end of the shaft for opening and closing the jaw, the method comprising the steps of:

closing the jaw using the hand mechanism;

inserting the shaft of the instrument into the patient;

penetrating tissue with the distal end of the shaft;

opening the jaw;

positioning the opening in the shaft proximate a piece of suture disposed in the patient;

closing the jaw to capture suture within the opening; and pulling the instrument with the captured suture back through the tissue.

20. The method of claim 19, further comprising the step of locking the jaw in a closed position during insertion of the shaft into the patient.

21. The method of claim 19, further comprising the step of sliding the captured suture into a notch in the distal face of the opening while pulling the instrument with the captured suture back through the tissue.

22. The method of claim 19, wherein the distal end of the shaft terminates in a sharp tip, and the step of penetrating tissue comprises piercing the tissue with the sharp tip.

\* \* \* \* \*